United States Patent [19]

Preikschat

[11] 4,107,599
[45] Aug. 15, 1978

[54] ELECTRODE FOR AN IMPEDANCE MEASURING APPARATUS

[76] Inventor: Fritz K. Preikschat, 16020 Lake Hills Blvd., Bellevue, Wash. 98008

[21] Appl. No.: 731,756

[22] Filed: Oct. 12, 1976

Related U.S. Application Data

[60] Continuation-in-part of Ser. No. 483,094, Jun. 26, 1974, Pat. No. 3,992,665, which is a division of Ser. No. 395,736, Sep. 10, 1973, Pat. No. 3,824,461, which is a division of Ser. No. 299,133, Feb. 24, 1972, Pat. No. 3,781,671.

[51] Int. Cl.² ............................................. G01R 27/26
[52] U.S. Cl. ................... 324/61 R; 294/73
[58] Field of Search ............ 324/61 P, 61 QS, 61 QL, 324/61 R; 294/73

[56] References Cited

U.S. PATENT DOCUMENTS

| | | | |
|---|---|---|---|
| 2,043,241 | 6/1936 | Eyer | 324/61 R |
| 2,759,147 | 8/1956 | Stein | 324/61 P |
| 2,829,341 | 4/1958 | Gietter | 324/61 P |
| 3,051,894 | 8/1962 | Fathauer | 324/61 R |
| 3,081,429 | 3/1963 | Moe | 324/61 R |
| 3,090,004 | 5/1963 | Breen et al. | 324/61 R |
| 3,559,052 | 1/1971 | Fathauer | 324/61 R |
| 3,566,260 | 2/1971 | Johnston | 324/61 R |
| 3,681,685 | 8/1972 | Tarry et al. | 324/61 QS |
| 3,739,264 | 6/1973 | Resh | 324/61 R |
| 3,760,267 | 9/1973 | Williams | 324/61 R |

FOREIGN PATENT DOCUMENTS

| | | | |
|---|---|---|---|
| 152,973 | 3/1963 | U.S.S.R. | 324/61 P |

*Primary Examiner*—Stanley T. Krawczewicz
*Attorney, Agent, or Firm*—Christensen, O'Connor, Johnson & Kindness

[57] ABSTRACT

An electrode, forming a part of an apparatus for measuring the electrical impedance of a variety of sampled materials for the purpose of determining moisture content, is composed of a pair of spaced-apart conductors across which an electrical field is radiated. In a first embodiment, useful for a sample of grain or the like, the electrode comprises a box including a flat central electrode plate vertically mounted within and electrically isolated from the enclosing grounded walls of the box. In a second embodiment, adapted for stacked tissue paper or the like, the electrode comprises a pair of opposed plates, both of which are electrically driven by a sensing circuit. In a third embodiment, particularly suited for wood chips, the electrode comprises a front opening box including a flat central electrode plate mounted on and electrically isolated from a grounded backing plate. The forward walls of the box are pivotally mounted at the top of the backing plate so that the lower end of the box opens outwardly to ensure complete dumping of the sampled material. In a fourth embodiment, used for stacked lumber as it dries in a kiln, the electrode is provided by an elongated cylindrical rod which is inserted into the center of the stacked lumber, with the walls of the kiln or the rails supporting a car having the lumber stacked thereon, normally being formed from a metallic material, serving as grounded conductors.

17 Claims, 8 Drawing Figures

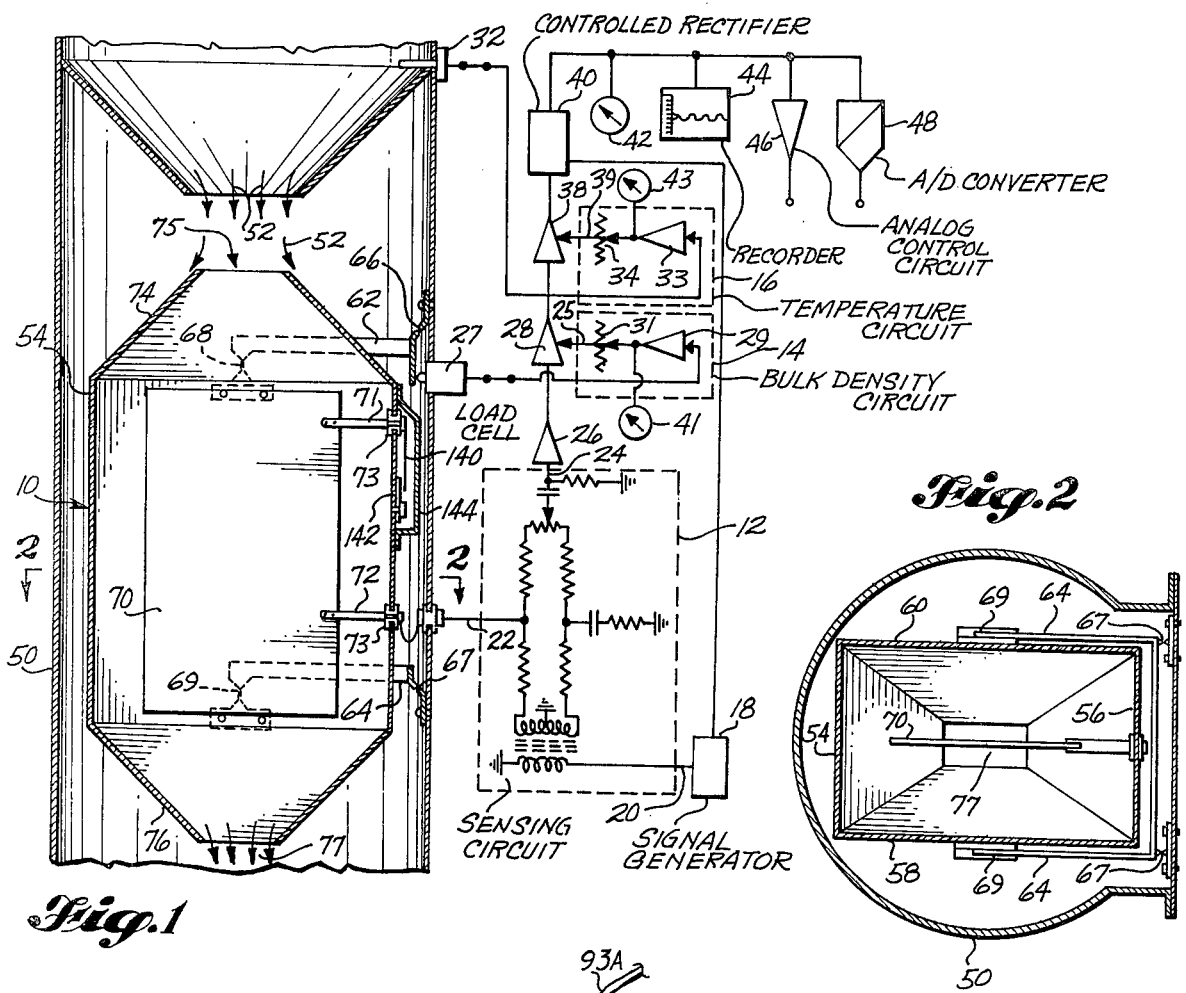

ELECTRODE FOR AN IMPEDANCE MEASURING APPARATUS

CROSS REFERENCE TO RELATED APPLICATIONS

This application is a continuation-in-part of application Ser. No. 483,094, filed June 26, 1974 entitled Electrical Impedance Measuring Apparatus, now U.S. Pat. No. 3,992,665, issued Nov. 16, 1976 which application is a division of my prior application Ser. No. 395,736, filed Sept. 10, 1973, now U.S. Pat. No. 3,824,461, issued July 16, 1974, which application is a division of my prior application Ser. No. 299,133, filed Feb. 24, 1972, now U.S. Pat. No. 3,781,671, issued Dec. 25, 1973.

BACKGROUND OF THE INVENTION

1. Field of the Invention

This invention related to apparatus for measuring the electrical impedance of materials, and in particular relates to a contoured electrode, a part of the apparatus for measuring the electrical impedance of material, shaped to accommodate different types of sample material in order that the electrical field radiated by the electrode passes through a sufficient portion of material sample enhancing the accuracy of the impedance measurement.

2. Description of the Prior Art

Optimizing the yield of various manufacturing processes often requires very accurate monitoring of the moisture content of a given material. For example, the milling of wheat is carried on most efficiently when the wheat has a 15% moisture content. During the pulping of wood chips, the moisture content of the wood chips must be known in order to determine the proper amounts of liquor necessary to be added for maximum delignification. The required accuracy for the measurement of moisture varies for different materials and is shown below for some representative materials:

| Material | Moisture Range | Typical Accuracy of Moisture Reading |
|---|---|---|
| Wood Chips | 30%-70% | ±2% |
| Wheat | 8%-15% | ±0.2% |
| Paper | 5%-10% | ±0.5% |
| Plywood Veneer | 3%-8% | ±0.5% |
| Potato Chips | 12%-17% | ±0.5% |
| Lumber | 30%-70% | ±3% |
| Tissue paper | 3%-10% | ±0.5% |

The disclosures in the above-identified related patents should be consulted to put the instant invention in perspective, and for an in-depth description of the component parts of a moisture detection system.

In order to make electrical impedance measurements of a sample material with the degree of accuracy necessary to determine moisture content, it has been found that it is desirable to construct the electrode to accommodate the different characteristics of the material to be sampled. For example, particulate materials of relatively uniform size and shape, such as grain or the like, are normally free flowing and are not subject to blocking when flowing through an area confined by an impedance measuring electrode. Other materials, such as corn fibers, potato chips and wood chips, are not nearly so free flowing, and it has been found that additional handling systems are generally desirable to pack the material and to transport it past the impedance measuring electrode.

The flow problem associated with the material to be sampled is particularly acute with wood chips, since, unlike grain, the size and shape variations in the chips tend to cause "bridging" as they pass the impedance measuring electrode. Sticky wood chips, such as those freshly cut during the early summer months, have an even greater then normal tendency to "bridge" or lodge in a sample box which also functions as an impedance measuring electrode.

A more exhaustive discussion of the problems associated with wood chips moisture measuring apparatus may be found in an article entitled "Factors Affecting Automatic Wood Chip Moisture Measurement" by F. K. Preikschat, Ekhard Preikschat and Daniel F. Pope, published in *Paper Trade Journal* dated July 29, 1974. This same article also describes a sample box suited for use with wood chips including a clam shell door at the lower end of the sample box.

In some manufacturing operations, such as pulp manufacturing, the bulk density measurement of the wood chips can be as important as a determination of the moisture content. Regardless of what type of digester is used in the pulping operation, the wood chips often are initially measured on a volumetric basis which means that in order to determine the total weight of chips entered into the digester the bulk density must be known. If both the moisture content and the bulk density of the wood chips in the material are known, these factors can then be used to determine the correct amount of liquor that is needed for the digester process itself.

In the digester process, it turns out that the wood to liquor ratio is one of the most important control parameters. The reason for this is that in order to obtain an optimum delignification, i.e. a dissolution of the lignin bonding the wood fibers, a certain amount of liquor has to be added to a given amount of wood chips to obtain an optimum delignification with minimum destruction to the wood fiber itself. Typically, the moisture content of the wood chips can vary over a 30% moisture range which is typically 35% to 65%. By the same token, the bulk density can also vary tremendously as determined by the size distribution of the wood chips, wood species, the type of chips used, e.g. core wood or sap wood, and the type of growth conditions encountered. Since there are so many variables involved, once the wet weight bulk density is related to the moisture content of the wood chips, it has been found that the bulk density may still vary over a considerable range. For example, under Southern growth conditions, it has been found that even though the moisture content does not vary by more than 4%, the bulk density can still vary by more than ± 15%.

Furthermore, wood chips are not homogeneous and even those in the same pile can differ widely in their physical makeup. Chips are produced from individual trees, which themselves are trucked to a common point from a wide surrounding area. If the moisture and bulk density of the chips contained in a storage pile were measured, both the moisture and bulk density would vary in a random fashion. Most often these parameters follow a normal distribution curve having an average deviation in moisture of ± 15% and an average deviation in bulk density of about ± 25%.

In the case of a continuous digester, wood chips and liquor are added in predetermined amounts simultaneously and continuously so as to produce a pulp of a certain quality. Here again, wood chips are added on a volumetric basis, as measured by the revolutions of the star feeding valve. The star feeding valve has a certain number of pockets, each with a given volume which makes it possible to readily calculate the volumetric feeding rate. If the wet weight bulk density of the wood chips is known, the volumetric feeding rate of the star valve can readily be translated into a wet weight flow of chips. This, in conjunction with the known or measured moisture content, can be translated into a bone dry weight flow of chips.

A more detailed discussion of pulp processing methods and the effects of variations in moisture content and bulk density may be found in an article entitled "Comparison of Pulping Methods" by Burton E. Helberg et al., published in *TAPPI*, Vol. 59, No. 5, May 1976.

In some manufacturing, a moisture control test may be used to ensure quality of an end product by measuring the moisture content to determine if it is within predetermined limits. For example, it is important that facial tissue when shipped from the manufacturer have a moisture content which does not exceed predetermined limits. At present, the moisture content of facial tissue is normally determined on a spot check basis. However, it would be desirable if all rolls or stacks of tissue paper could be checked for moisture content on a continuous basis prior to packaging and shipping without adding significantly to production cost.

Still another application where it is desirable to accurately measure moisture content is in the drying of lumber. One method of drying lumber involves positioning the rough cut wood in a closed heated structure, such as a kiln or the like, for a period of from 1 to 5 days. The drying rate is not a constant but depends on a number of variables such as the type of lumber, initial moisture content, temperature within the kiln, etc. Presently there is no reliable way to measure the drying rate or to determine the point during the drying cycle at which a desired amount of moisture has been removed from the wood. A more precise and accurate measurement of moisture content during this drying cycle is important for several reasons. First, the cost of energy and heating in recent years has increased dramatically and it has become economically imperative that the drying time be kept to a minimum. Second, when wood is overdried it becomes very difficult to work with wood working machines, such as lathes and planers, further increasing lumber production costs. Under current practice, if lumber has been overdried, it is often rewetted in order to raise its moisture content to approximately 10%.

One known method of ascertaining dryness presently used by kiln operators involves manual spot checking of the moisture content of indivdual pieces of lumber in the kiln. This procedure involves the use of a two-prong resistance gauge which is pressed against the surface of a piece of lumber to determine surface resistance. This resistance reading is then related to moisture content via a chart or formula. Inaccuracies are inherent in this method since the resistance reading on the gauge can vary depending on the amount of contact pressure, the temperature of the wood, the surface properties of the wood, and its position in the stack, in addition to the moisture content of the lumber itself.

SUMMARY OF THE INVENTION

The present invention discloses apparatus for determining moisture content of a variety of samples of materials by accurately measuring the electrical impedance of the material sample. The present invention is particularly concerned with shaped sensing electrodes which are sized and contoured to accommodate the varying characteristics of the material being sampled so that the electrical field radiated by the electrode passes through a substantial portion of the material sample enhancing the accuracy of the impedance measurement.

In an embodiment of the instant invention particularly suited for measuring the impedance of a sample of wood chips in order to determine its moisture content, the electrode is shaped as a novel sample box in which the wood chips are deposited. A unique dumping system eliminates any tendency of the wood chips to hang up or bridge against the side walls of the sample box. A mechanically integrated system incorporating a particularly shaped outer grounded electrode and an active central electrode plate also includes a means for measuring both the temperature and weight of the sample of material so that the output of a sensing circuit connected to the electrode can be corrected to reflect both temperature and weight variations.

According to yet another aspect of the instant invention, a bulk density circuit and a temperature circuit for a sample box are each provided with a direct readout device so that the bulk density and temperature of the sample of material within the constant volume defined by the sample box can be visually observed and utilized in the processing of the sample of material.

BRIEF DESCRIPTION OF THE DRAWINGS

FIG. 1 is a sectional elevation of a first embodiment of a shaped electrode according to the instant invention usable with free flowing material, such as grain, and including a schematic diagram of an impedance sensing circuit.

FIG. 2 is a sectional view of the shaped electrode taken along line 2—2 in FIG. 1.

FIG. 3 is a second embodiment of a shaped electrode according to the instant invention particularly suited for measuring the electrical impedance of stacked paper or the like.

FIG. 4 is a schematic diagram of a sensing circuit usable with the electrode embodiment of FIG. 3.

DETAILED DESCRIPTION OF THE PREFERRED EMBODIMENTS

Figure 5:
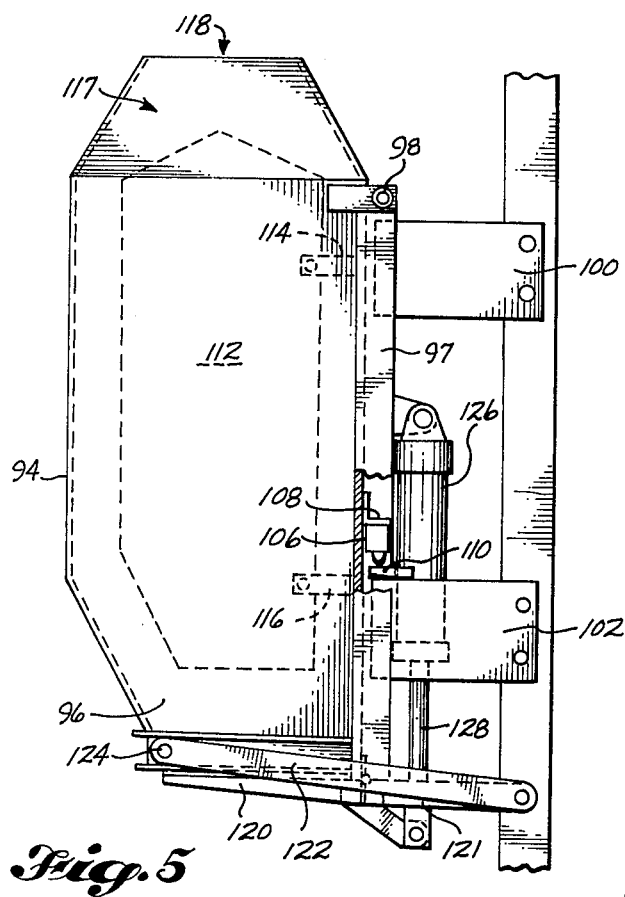
FIG. 5 is a side elevational view of a third embodiment of a shaped electrode according to the instant invention particularly suited for measuring the electrical impedance of bulk materials, such as wood chips.

Referring initially to FIG. 1, a first embodiment of an electrode 10, made according to the teachings of the instant invention, is illustrated as part of an apparatus for measuring the impedance of a sample of material and, in turn, relating this impedance to a characteristic of the material, such as its moisture content. In addition to electrode 10, the system includes a sensing circuit 12, a bulk density circuit 14 responsive to weight variations and a temperature circuit 16. A signal generator 18 is connected to sensing circuit 12 by lead 20 and supplies a stabilized reference signal of a certain frequency and phase. Sensing circuit 12 is also connected to the active portion of electrode 10 by lead 22 and provides a high frequency electrical signal which creates a high frequency electrical field in the material whose impedance is to be measured.

Although described in greater detail in the above-identified parent patents, the output signal from sensing circuit 12 is directly proportional to the moisture content of the sampled material when properly corrected for variations in temperature and bulk density, if necessary. Thus, the output of sensing circuit 12 is connected via lead 24 and amplifier 26 to operational transconductance amplifier 28. Amplifier 28 includes a control input lead 25 which varies the amplification factor of the amplifier. A load cell 27 provides a continuous output signal which is proportional to the weight of the fixed volume of materials situated within electrode 10. The output signal from load cell 27 is connected to bulk density circuit 14. In preferred form bulk density circuit 14 comprises an amplifier 29 and an adjustable voltage divider 31. In operation, amplifier 28 multiplies the output signal from sensing circuit 12 by the output signal from bulk density circuity 14 in amplifier 28 so that the signal at the output of amplifer 28 is corrected for bulk density variation of the sample material by bulk density circuit 14.

In a similar manner, the moisture measuring system for grain also includes a temperature circuit to compensate for temperature variation in the sample material. In preferred form, temperature circuit 16 comprises an amplifier 33 which is connected to a variable voltage divider 34. An operational transconductance amplifier 38 includes a control input lead 39 which varies the amplification factor of amplifier 38. A temperature sensor 32 is connected to the input of amplifier 33 and provides a continuous output signal which is proportional to the temperature of the sample material situated within the sample box. In operation, amplifier 38 multiplies the output signal from operational amplifier 28 by the output signal from temperature circuit 16 to compensate for variation in the temperature of the sample material.

An important aspect of the present invention is that static bulk density and temperature of the sample material can be directly read and used, if required, in a manufacturing process. A display device 41, preferably calibrated in bulk density per cubic foot, is connected to the output of amplifier 29 of bulk density circuit 14. A temperature display device 43, preferably calibrated in ° C or ° F, is connected to the output of amplifier 33 of temperature circuit 16. This allows these parameters to be read directly when the sample material is being utilized in a manufacturing process.

After the output signal of sensing circuit 12 is corrected for variations in temperature and bulk density, the combined signal is finally rectified in rectifier 40 and the resulting DC output signal is read on one or more of several output devices such as meter 42, recorder 44, analog control circuit 46 or A/D converter 48, the latter two being capable of providing an input to other devices. It should again be understood that a more extensive and detailed discussion of the actual operation of the hereabove described electrical circuits is provided in the hereabove-identified parent patent disclosures.

Referring additionally to FIG. 2, a first embodiment of a contoured electrode for an impedance measuring device, particularly adapted to be used with free flowing particulate material, is illustrated. In order to make accurate impedance measurements, the impedance measuring electrode must be sized and shaped both to accommodate the varying properties of the material to be sampled and to create an electrical field, in operation, which passes through almost all of the sample material in the sample box. In preferred form, this embodiment includes an outer electrode which is shaped as a box or container having a rectangular cross section. as illustrated, the box is preferably positioned within a sampling tube 50 in which grain is continously flowing in a downward direction as indicated by arrows 52. The sample box comprises front wall 54, rear wall 56 and side walls 58 and 60. The sample box is supported in an upright position by upper U-shaped arm 62 and lower U-shaped arm 64 which are themselves mounted on the wall of sample tube 50 by means of a pair of upper support brackets 66 and lower support brackets 67. As illustrated, each pair of support brackets 66 and 67 comprise short pieces of resilient material such as piano wire mounted to extend between its support arm and the side wall of tube 50. The outwardly extending ends of each pair of arms 62 and 64 are connected to side walls 58 and 60 by means of a pair of mountings 68 and 69. Each of these mountings allows the sample box to flex or vibrate in a vertical direction. As is best seen in FIG. 2, each support arm 62 and 64 has a relatively narrow top surface area thereby reducing dust accumulation thereon which would possibly falsify the weight reading obtained by load cell 27.

As is best seen in FIG. 2, center electrode plate 70 is vertically disposed within the sample box in parallel spaced relation to side walls 58 and 60. Upper rod 71 and lower rod 72, each including an insulating bushing 73, support center electrode plate 70 along the center line of the sampling box.

An important aspect of the present invention is that the sample box is sized and shaped to cooperate with the natural flow characteristics of particulate material, such as grain and still provide a spaced-apart pair of conductors which are positioned to radiate an electrical field into substantially all of the sample material in the sample box. A top portion 74 of the sample box is integrally connected with the front, rear and side walls and, at its upper end, defines an opening 75 which is the inlet of the sample box. At the opposite end of the sample box, a bottom portion 76 is formed by an inwardly inclined wall, also integrally connected with the sample box walls. Bottom portion 76 converges to an opening 77 at the low end of the box which defines an outlet for the sample box. Outlet opening 77 in bottom portion 76 is slightly smaller in area than the inlet opening 75 at the top of the sample box. As should be apparent, once the sample box is filled, it is maintained in a constantly filled to overflowing condition, and at the same time, the contents of the sample box are continuously changing so that repetitive impedance measurements reflect the moisture variation in the sample stream. Excess sample material passes downwardly over the outside walls of the sample box. To enhance this flow pattern, top portion 74 is inclined at an angle which is steeper than the normal angle of repose of the sample material funneled thereto. This assists in maintaining the sample box filled such that a substantially constant volume of material with a uniform packing density related to the drop height of the grain is obtained. Accordingly, there is a continuous output signal from load cell 27 related to the weight of the sample box, and this signal is proportional to the bulk density of the material in the sample box.

Another feature of the electrode configuration according to the instant invention is that a minor mechanical or geometrical deviation in the sample box has a small effect on the electrical field radiated through the sample material and, hence, minimal effect on the impedance measurement. For example, while electrode plate 70 is mounted substantially along the center line of the sample box, it should be understood that small lateral displacements will not cause a significant change in the capacitance because the larger capacity on one side of the electrode will be compensated by an accordingly smaller capacity on the opposite side.

Referring now to FIG. 3, a second embodiment of a shaped electrode according to the instant invention, particularly well suited for use with stacked material such as tissue paper or the like, is dislocsed. In this embodiment, a first electrode plate 79, comprising a flat planar member, is positioned on edge so that its plane extends essentially in a vertical direction. A second electrode plate 80 is laterally spaced from the first plate and is also disposed on edge so that its surfaces extend along a second vertical plane which is substantially parallel to the plane of first electrode plate 79. The first and second electrode plates 79 and 80 are held in their spaced relationship by a U-shaped mounting braket 81, fabricated from an electrical insulating material having a pair of downwardly extending arms on which the electrode plates are mounted. The sample material is passed, such as by a conveyor belt, through the area between the electrode plates so that its electrical impedance can be measured by sensing circuit 82.

Rather than an active and grounded electrode as described in conjunction with the first embodiment of the invention, in this second embodiment of a shaped electrode, both first electrode plate 79 and second electrode plate 80 are electrically active or driven in the sense that neither plate, in operation, is connected to ground. Referring now to FIG. 4, one form of sensing circuit 82 is illustrated which is particularly adapted for use with parallel plate electrode configurations. A sensing circuit 82, for reasons of convenience, can be mounted on bracket 81 and is connected via leads 83 and 84 to first and second electrode plates 79 and 80, respectively. An impedance including variable capacitor 86 is connected to lead 84 so that any variation in capacitance between electrode plates 79 and 80, resulting from geometric variations in the plates or the influence of external objects, can be equalized by adjustment of the capacitor. A signal generator (not shown) provides a test signal to the sensing circuit input and transformer 85. In preferred form, sensing circuit 82 is of a bridge design for use with an electrode assembly having two active plates. Resistors 87 and 88 comprise one leg of the bridge and first electrode plate 79 is connected via lead 83 between the resistors. Resistors 89 and 90 comprise the other leg of the bridge with second electrode plate 80 connected therebetween via lead 84. The bridge assembly itself is inherently stable and symmetric so that each of the electrodes is separately driven to provide equal but oppositely phased field amplitudes in the area between the electrode plates.

The electrical signals to each leg of the bridge are of equal but opposite polarity and the outputs from resistors 88 and 90 are connected via leads 91 and 92, respectively, to the input of a comparator circuit 93. The output signal 93A from comparator circuit 93 will then be directly porportional to the impedance of the sample material.

In operation, sample material is positioned on the conveyor belt so that it will pass between parallel electrode plates 79 and 80. When the sample material, such as a plurality of stacked sheets of tissue paper, has moved along a conveyor belt so that the mid-point of the material to be sampled is approximately intermediate the electrode plate, a reading from sensing circuit 82 is taken, preferably controlled by an automatic position sensing device such as a photoelectric eye or the like. The electrical output signal 93A from sensing circuit 82 is directly proportional to the impedance of the sample material, and, in contrast to the moisture measuring system heretofore described for grains, it is normally unnecessary to correct the output signal for temperature and weight variations. Temperature correction is in most cases unnecessary since the ambient temperature in the area where the paper is being processed is relatively constant and the material sample temperature is stabilized at this ambient temperature. This allows a constant temperature correction factor to be used eliminating the necessity of individual compensation for each sampling.

A constant correction factor could also be introduced into the electrical output signal to compensate for bulk density. For example, a given sample material, such as a stack of tissue paper, has a size and bulk which is essentially a constant, and hence, its bulk density would be constant so that the output signal 93A from sensing circuit 82 can be initially set for a known bulk density dependence, so long as the type and size of the material sampled does not deviate significantly.

Furning now to the third embodiment of a shaped electrode according to the instant invention, this embodiment is well-suited for use with a system for measuring the moisture content of irregularly shaped sample material such as wood chips. As indicated herebefore, impedance measuring devices which are particularly adapted for ascertaining the moisture content of wood chips normally require an electrode geometry which differs from that used with particulate materials such as grains. For example, wood chips, unlike grains, are not free flowing and have a tendency to "bridge" or become wedged together while flowing, and this tendency is more acute if the chips are required to flow through a constrained passageway. For this reason, it has been found that it is desirable that the sampling be done on a discrete or non-continuous basis, such as by consecutively filling a sample box, ascertaining the necessary characteristics of the sample after each filling, and then discharging or exhausting the material. Also, it has been found that the discharge action should be very positive to break down any tendency of the wood chips to bridge or hold together during the sampling procedure so that each discrete sample will be completely exhausted from the sample box before the next measuring operation is started. Finally, the component parts of the measuring system which interact with the material sample, such as the load cell, temperature sensor, suspension system, etc., should be built into a basic support frame so that the entire system is integrally combined into a single unit, except possibly for some of the electrical circuitry, to simplify the overall mechanical installation of a wood chip moisture measuring system.

Figure 6:
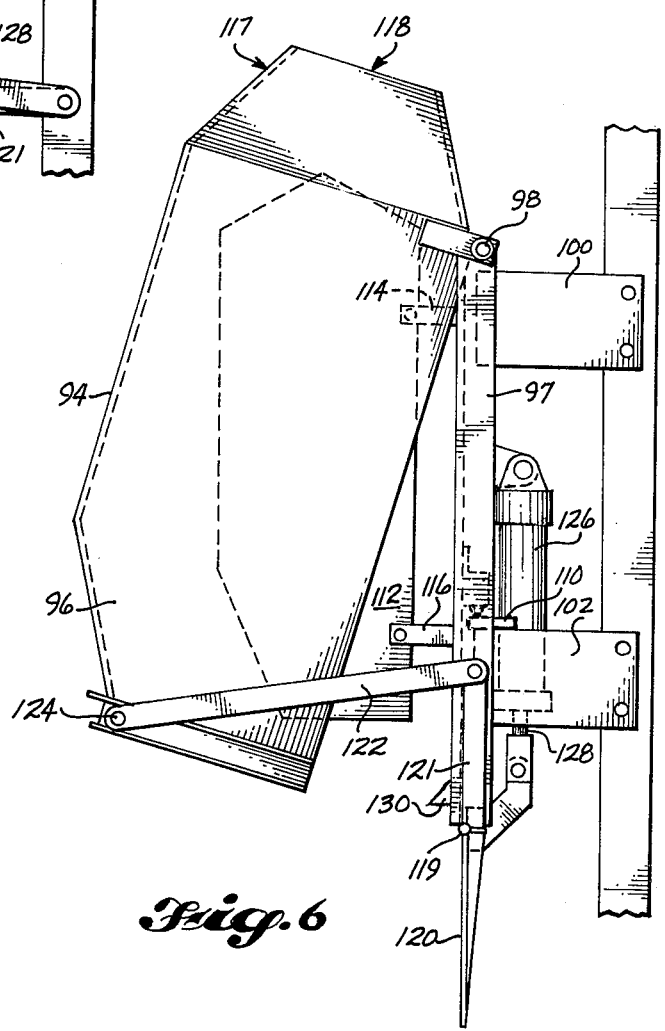
FIG. 6 is a side elevational view of the electrode of FIG. 5 but with the sample box shown in an open position.
Figure 7:
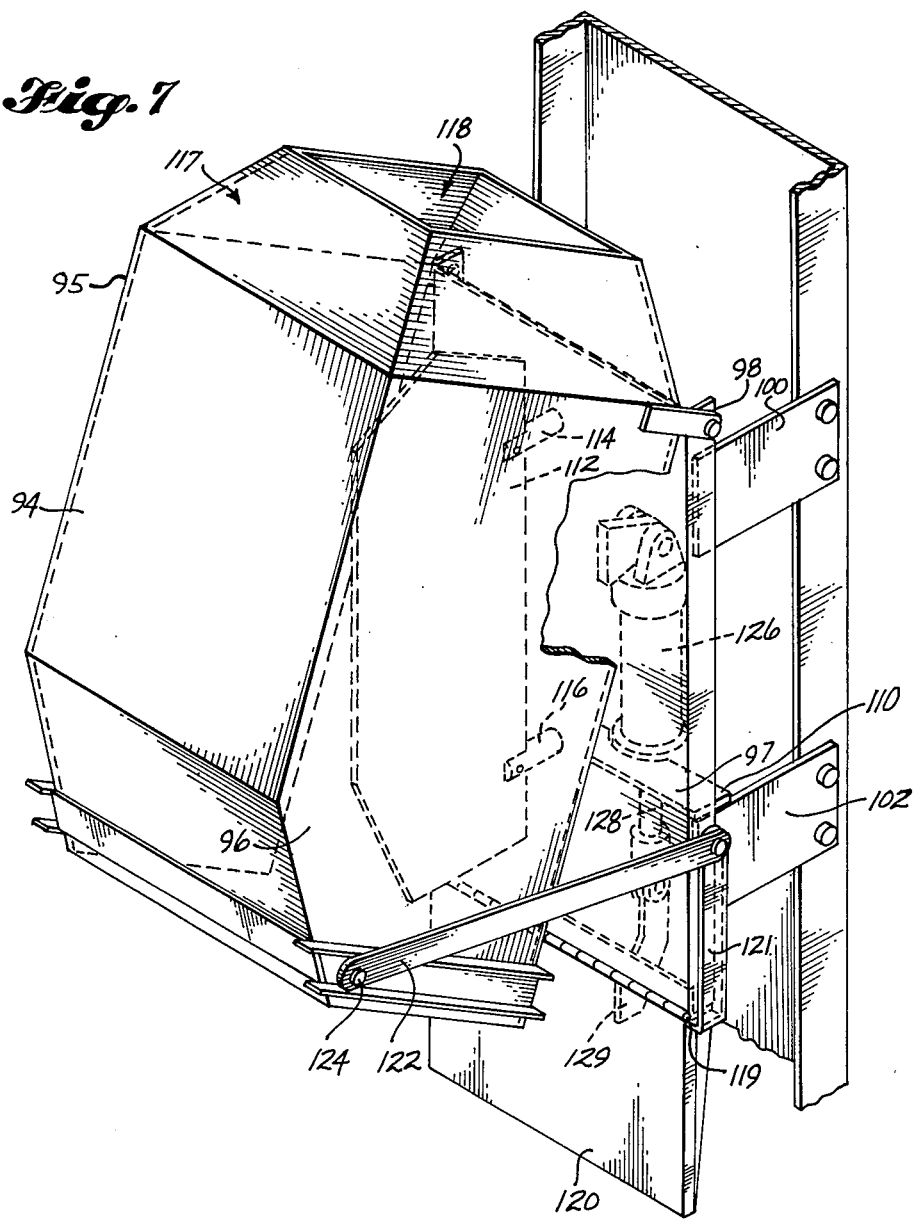
FIG. 7 is a perspective view of the electrode of FIG. 6.

Now referring to FIGS. 5-7, the third embodiment of the electrode is shown to include a grounded portion which is shaped as a box or container having a rectangular cross section so that, if desired, it may be positioned in a stream of sample material in the same manner as the sample box of FIG. 1. This sample box comprises front wall 94, side walls 95 and 96, and backing plate 97, together forming the closed walls of a rectangular container. Front wall 94 and side walls 95 and 96 are preferably integrally connected and pivotally mounted near the upper end of backing plate 97 by a pair of pin joints 98. The sample box is supported in an upright position by a pair of upper brackets 100 and lower brackets 102 which are themselves mounted on a vertical wall or other rigid structure adjacent the flow path of the sample material. A main support frame (not shown) attached behind backing plate 97 is fixedly mounted to upper and lower support brackets 100 and 102 forming a laterally extending framework for supporting backing plate 97 to which is mounted a portion of the electrical circuit components of the moisture measuring system, these components being similar to those described in conjunction with the first embodiment.

As is seen in FIG. 5, a load cell 106, part of the bulk density circuit, is directly built into the basic suspension frame of the sample box to simplify the overall mechanical installation. In preferred form, load cell 106 is fixedly attached by a bracket 108 to backing plate 97 of the sample box. Load cell 106 is positioned so as to bear against a bar 110 which is rigidly mounted on and extends laterally between the lower mounting brackets 102. Backing plate 97 is held in a vertical position by the main support frame and a set of upper and lower springs (not shown) mounted to extend laterally between the support brackets. The steel springs are sufficiently flexible to allow unimpeded vertical motion of backing plate 97 with respect to the main support frame, so that substantially all of the weight of the sample box is supported by load cell 106 as it bears against bracket 110.

An active center electrode 112 is vertically disposed within the sample box in parallel, spaced relationship to side walls 95 and 96 so that a uniform electrical field is created during operation of the impedance measuring apparatus which passes through substantially all of the material sample. Upper rod 114 and lower rod 116, together with an insulating bushing (not shown), support center electrode plate 112 along the approximate center line of the sample box. A top portion 117 of the sample box is preferably integrally formed with front wall 94 and side walls 95 and 96 such that it extends inwardly creating an inclined wall which, at its upward end, defines an opening 118, the inlet to the sample box.

At the lower end of the sample box, a hinge 119 is secured on backing plate 97 and mounts trap door 120 for pivotal movement between an open and closed position. In the closed position, as illustrated in FIG. 5, trap door 120 extends horizontally from backing plate 97 closing the outlet of the sample box. As is seen in the drawings, front wall 94 is tapered or inclined inwardly at its lower end, both to give the three wall configuration forming the pivoting member additional rigidity and to reduce the size of trap door 120. Additionally, this inward tapering reduces the outward extent of movement of front wall 94 in the open position (FIGS. 6 and 7) thereby reducing the forward clearance required during the discharge of the sample material.

As indicated herebefore, a desirable feature of a discrete sampling system for measuring moisture in wood chips is that the sample box have a positive action during the exhaust cycle to break any bridging tendency. Accordingly, the sample box of the instant invention pivots at its upper end to open outwardly thereby causing a sudden relative movement between center electrode 112 and side walls 95 and 96. To cause this pivotal action, one end of each of a first pair of linkage arms 121 is fixedly attached to either side edge of trap door 120. The opposite end of each first linkage arm 121 is pivotally attached to one end of a pair of second linkage arms 122. As illustrated, the outward end of each linkage arm 122 is pivotally secured to the forward portion of each side wall by a pair of laterally extending pins 124. As is apparent by a comparison of FIGS. 5, illustrating the sample box in its closed position, with FIGS. 6 and 7, illustrating the box in its open position, movement of trap door 120 from its horizontal or closed position to a vertical or open position causes, through linkage arms 121 and 122, outward movement of the front and side walls of the box thus dislodging the sample material in the sample box.

The mechanical force required to move the sample box between its open and closed position is provided by an actuating means 126. In preferred form, actuating means 126 is mounted on backing plate 97 and includes a control rod 128 which is pivotally attached at its outward end to door extension arm 129, the opposite end of which is fixedly mounted on the underside of trap door 120. Movement of control rod 128 between its end positions causes both pivotal movement of trap door 120 between its vertical and horizontal orientation and outward movement of the lower portion of the sample box via linkage arms 121 and 122. In preferred form, actuating means 126 is a pneumatically actuated cylinder and piston but is should be understood that other types of actuating means such as a hydraulic cylinder and piston or an electric solenoid or the like, could also be used.

As is best seen in FIG. 6, a temperature sensor 130, preferably a thermistor, is mounted on backing plate 97 above trap door 120 so that it projects outwardly for maximum contact with the sample material received within the sample box. In the same manner as discussed herebefore with regard to the first embodiment, temperature sensor 130 is electrically connected to a temperature compensating circuit for correcting the output signal of the sensing circuit so that the sensing circuit output signal is corrected for variations in the material sample temperature. The outwardly projecting portion of the sensor is preferably triangularly contoured for maximum contact with the wood chips. It is preferably fabricated from a material, such as phosphor bronze, which has a high heat conductance coefficient thus minimizing the inaccuracies associated with temperature compensation by minimizing hysteresis or time lag associated with the transfer of heat flux from the material sample to the thermistor. Heat transfer is particularly important because the wood chips may only contact the projecting triangular surface of the temperature sensor at a limited number of points and the wood itself is a poor conductor of heat.

In operation, the sample box is mounted on a vertical support so that wood chips may be received into inlet opening 118 in top wall 117. Wood chips for sampling are often diverted from a main flow stream and may be brought to the sample box in any of a number of ways including a conveyor belt, blown via air pressure through an air duct, or merely shoveled by hand into the sample box inlet. When the sample box is full, an electrical impedance measurement is taken by a sensing circuit in the same manner as heretofore described in conjunction with the embodiment of FIG. 1. With center electrode plate 112 disposed between side walls 95 and 96, a uniform electrical field of substantially constant strength passes through almost all of the wood chips in the sample box. If necessary, the electrical output signal from the sensing circuit is weight compensated by a bulk density circuit and temperature compensated by a temperature circuit in the manner heretofore described. If disposed in a stream of wood chips such as from a conveyor belt, this sampling operation and the cycling of the sample box may be operated by an automatic control device such as a timing means or photoelectric cell oriented to determine when the sample box is filled to overflowing. After the impedance measurement is taken, actuating means 126 is cycled, thereby causing the front and side wall portion of the sample box to pivot outwardly, and trap door 120 to open, to exhaust the wood chips from the sample box. After a sufficient period of time for the wood chips to drop clear of the sample box outlet has passed, the push rod of actuating means 126 is returned to its opposite end position closing the sample box and completing the measuring cycle.

As mentioned herebefore, an important aspect of the instant invention is that the bulk density and temperature of a sample of material can be read directly via display devices attached to bulk density circuit 14 and temperature circuit 16. It has been found that knowing these parameters is particularly important in some manufacturing operations such as pulp processing. For example, in a pulping operation the wood chips are digested by the action of a cooking liquor which dissolves the lignin in the wood thereby releasing the individual wood fibers. There are both batch and continuous types of digesters available, and both require that the wood chips and liquor be added in a predetermined ratio. With either the batch or continuous process, both the bulk density and moisture content of the wood chips must be known to ascertain the proper amount of liquor which must be added to optimize the wood chip-to-liquor ratio.

In the case of a continuous digester, wood chips and liquor are continuously added to the digester. A quantity of wood chips are added basically on a volumetric basis such as determined by a number of revolutions of a star feeding valve. As is known, such a star feeding valve has a certain number of pockets, each with a given volume so that the volumetric feed rate into the digester inlet can be readily calculated. Accordingly, if the wet weight bulk density of the wood chips is known, as indicated by display device 41, the volumetric feed rate of the star valve can be readily translated into a wet weight flow measurement of wood chips. This parameter, in conjunction with the moisture content measurement of the wood chips, can be converted into a dry weight flow of wood chips. Finally, this calculation of the dry weight of wood chips is used to determine the amount of liquor which must be added to the digester.

As pointed out above, the reading on display device 41 indicating the wet weight bulk density is a primary factor for optimizing the operation of the digester. Bulk density is defined as the weight per unit of volume and in the case of wood chips depends on a number of variables including wood species, size distribution of the chip particle, and the amount of settling between the larger and smaller pieces. Wood chips are of nonuniform size and a given volume of wood chips is to some degree compressible depending on the extent that the normal handling of the chips has reduced the voids or air spaces between chips. In the situation where a flow of chips is fed from a number of different sources, each with a different bulk density and moisture content, there is no practical way to accurately determine the weight of a specific portion of the chip flow as the entire mass is transported by a bulk conveyor.

The inaccuracies inherently associated with the dynamic measurement of the bulk density of such a moving chip stream has led to the conclusion that this measurement is preferably ascertained by taking repetitive static measurements at successive points in the chip stream under conditions which are consistent between consecutive samples. With the instant invention, this is done by successively filling a sample box, taking both bulk density measurement and moisture content measurement of the contents of the sample box, and then exhausting the sample material from the sample box. One method of ensuring that the measuring conditions of repetitive samplings are uniform between consecutive samples is to drop the chips at a given rate, typically 12 inches, into the sample box so that the chip compaction factor will be the same for each measurement.

In most pulping operations, because of the large volume of wood chips required by the digester it is impractical to measure the bulk density and moisture content of the entire chip flow. Accordingly, the wood chips delivered to the sample box are only a fraction of the total chip flow so it is important to ensure that the wood chips actually deposited in the sample box reflect a cross section of the overall chip flow. Because of the inherent nonuniform size of the wood chips, a segregation often occurs during transportation and handling in which the smaller or fine chips tend to settle to the bottom of a chip flow. Accordingly, to obtain a representative sample from the chip flow, it is necessary to extract wood chips from all layers of a cross section of the primary flow. One method of ensuring a representative cross section is by installing a small sampling conveyor belt at a point where the chip stream is dropped into a chute. By intersecting the falling primary chip stream, the conveyor belt receives a representative sampling from the various layers of the primary chip flow. The flow from this smaller, sampling conveyor belt can then be used in the manner hereinbefore described to fill the sample box so that a bulk density and moisture content measurement can be taken.

As indicated herebefore, the embodiments of the shaped electrode according to the instant invention are particularly sized to compensate for the varying characteristics of material particles to be sampled and to radiate an electrical field through almost all of the material sample. For instance, a typical sample box forming the outer grounded portion of the electrode, as illustrated in the first embodiment for measuring the electrical impedance of particulate material, may have a volumetric capacity of approximately 24 cubic inches and a center electrode plate situated so that it is parallel to the side walls so that a uniform electrical field is radiated. In its preferred vertical orientation during operation, the free flowing properties of the grain are such that the particulate material passes easily through the sample box eliminating the need for additional material handling systems. However, in the case of wood chips, the sample box, as illustrated in the third embodiment of the instant invention, should have a capacity of at least 2 cubic feet to average out variations in chip size and to provide sufficient room on either side of the center electrode plate.

The sample box of the first and third embodiments discussed above forming the grounded electrode may be constructed of stainless steel having a relatively low thermal expansion coefficient of $10 \times 10^{-6}$ per °C., that is a change of $7 \times 10^{-4}$ for a 70° C. change in temperature. Capacitance is inversely proportional to the distance between the active electrode plate and the outer housing of the sample box which is grounded, and thus a sample box having a capacitance of 10 pF. is changed by less than 0.01 pF. for a 70° C. change in temperature. This change in capacitance may be ingnored except for cases where a very low moisture content is to be measured or where the material is fluffy and has a dielectric coefficient very close to one. The first embodiment of the sample box for particulate material has been adapted to compensate for this variation. As is seen in FIG. 1, the thermal drift is corrected for by mounting a bimetallic strip 140 on one of the support rods of the electrode to provide a small variable capacitance between the bimetallic strip and grounded electrode 142 attached to the rear wall 56 of the sample box. Thermal drift may then be offset by an opposing change of capacitance due to the motion of the bimetallic strip. This assembly is protected by a dust cover 144. However, in the wood chip embodiment of FIGS. 5–7, it has been found that the thermal expansion error is slight and no correction apparatus need be specifically attached to the sample box.

An alternate but more expensive solution is to construct a sample box and center plate electrode from a material such as Invar Steel which has a thermal expansion coefficient of only $0.8 \times 10^{-6}$ per °C. This construction reduces thermal drift by a factor of more than 10 compared to stainless steel.

Figure 8:
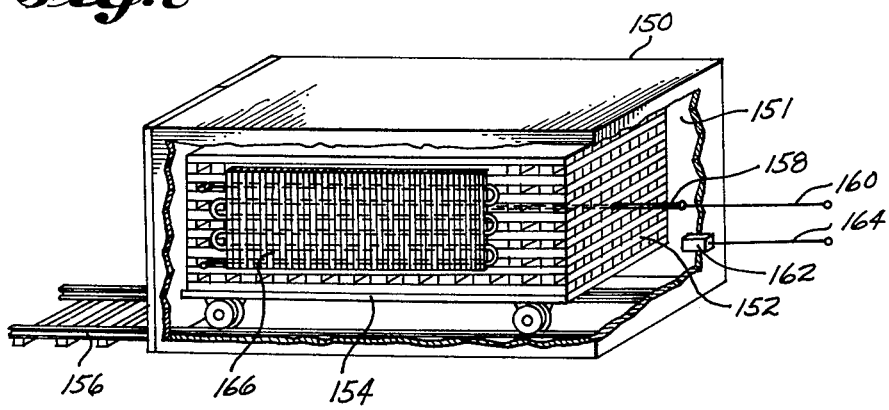
FIG. 8 is a perspective view of a fourth embodiment of a shaped electrode according to the instant invention particularly suited for measuring the electrical impedance of stacked lumber in a kiln.

Finally, turning to the fourth embodiment of the shaped electrode according to the instant invention, this embodiment is particularly well-suited for measuring the electrical impedance of sample material drying in a closed drying structure, such as a kiln or the like to determine its moisture content. As is seen in FIG. 8, a kiln 150 typically comprises an outer housing or wall defining a relatively large internal chamber 151 in which the sample material 152 is disposed during the drying cycle. Sample material 152 is often green lumber which has been rough cut and stacked on cart 154 so that it can be conveniently moved. Cart 154, with its stacked sample material thereon, can be pushed along a pair of rails 156 into internal chamber 151 of kiln 150. An axially elongated center electrode 158, having a length sized to extend approximately the length of the stack of lumber, is inserted into the approximate midpoint of the end face of the stack. In the same manner as heretofore described in connection with the embodiment of FIg. 1, a lead 160 is connected to a sensing circuit (not shown) which may be either at a remote location or attached to kiln 150. In any event, it is desirable to thermally insulate the sensing circuit from any fluctuating heat source such as the kiln, so that the electrical characteristics of the components of the sensing circuit will not be changed by the periodic heat variations. The sensing circuit provides a high frequency electrical signal to electrode 158 creating a high frequency electrical field which pass through the sample material, the impedance of which is to be measured.

In this embodiment, the walls or housing of the kiln 150, together with metal rails 156, act as a surrounding grounded electrode which cooperates with the center electrode in measuring the impedance of the material sample. Most kilns have sufficient metallic conductors in the walls and floors to act as an outer grounded electrode for impedance measurement, the component parts of such an impedance measuring system being as described both heretofore and in my prior related patents. A temperature sensor 162 is preferably provided and is connected via lead 164 to a temperature circuit (not shown).

In operation, when cart 154 containing the stacked lumber has been disposed within the closed internal chamber of kiln 150 and active electrode 158 inserted into the center of the stack, the drying cycle begins and the temperature in internal chamber 151 is raised by turning on heater 166. The high frequency electrical signal applied to central electrode 158 creates an electrical sensing field which passes through the stacked wood to the outer metal conductors in the walls and floor of kiln 150. Because of the large distance separating the inner and outer conductors, the exact location and external geometry of the active electrode 158 is not important so long as it is located aproximately near the center of the stacked lumber. For the case where the active electrode is a plain antenna rod, and the outer conductors are in the near vicinity of the stack of wood, the lineal capacitance between the two "electrodes" is given by:

$$C = \frac{7.4\, \epsilon}{\log_{10}(b/a)}\ pF/ft,$$

where $\epsilon$ is the dielectric constant (relative to air), $b$ is the distance between center and outer conductors, and $a$ is the radius of the center conductor. For the typical case, $\epsilon$ is between 1 and 2, and $b/a$ is between 100 and 10,000, in which case the lineal capacitance will vary over a range of 1.85 to 7.4 pF/ft., assuming the existance of a small air gap between the lumber stack and the outer conductors. Where there is a sizeable air gap the capacitance will be correspondingly reduced. Also, for an active conductor of small sized diameter, the ratio of $b/a$ can vary greatly without significantly affecting the measured capacitance. For the case where the ratio of $b/a$ is held fixed, the measured capacitance (or impedance reading) can be directly calibrated in average percent moisture and used as a set point control for terminating the kiln drying.

In the same manner as heretofore described, the electrical output signal from the sensing circuit is directly proportional to the moisture content of the sample material when properly corrected for temperature and bulk density dependency. Bulk density correction can be introduced as a constant factor since the amount of sample material stacked on each cart 154 and the type of lumber are known. As the drying cycle for the lumber begins, the elevated temperature in the kiln causes a moisture content decrease within the material sampled. In turn, this changes the dielectric coefficient between active electrode 158 and the passive grounded conductors of kiln 150, and this change is reflected by a proportional deviation in the output signal of the sensing circuit when corrected for temperature dependence. After the moisture content of the lumber has been reduced to approximately 10%, the drying cycle is complete and the lumber can then be removed from the kiln.

The invention may be embodied in other specific forms without departing from the spirit or central characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What is claimed is:

1. An electrode which is part of an apparatus for measuring the impedance of a sample of material, said electrode being formed as a sample box for receiving a sample of material through which an electrical field is radiated, comprising:
    front, rear and a pair of opposed, flat side walls of conductive material, together forming a rectangular container in which material to be tested is deposited;
    an inlet means situated at one end of said sample box, including an opening which is sized to receive a sample of material therethrough;
    an outlet means situated at the other end of said sample box, adapted to exhaust the sample of material after its electrical impedance has been measured; and,
    a flat electrode plate of conductive material mounted within said sample box and situated with its surfaces substantially parallel with and substantially equidistant from said opposed, flat side walls, said electrode plate being electrically insulated from the walls forming said sample box.

2. An electrode according to claim 1, wherein said outlet means of said sample box includes a door pivotally attached along one edge to the rear wall of said sample box, said door having a closed position substantially sealing the outlet of the sample box and an open position in which the sample material is exhausted from the sample box; an actuating means moving said door between its open and closed positions; the electrical impedance of the sample of material being measured with the door in its closed position.

3. An electrode according to claim 1, wherein said front wall and said pair of opposed, flat side walls are formed as an integral member pivotally mounted near its open side to said rear wall; and further comprising an actuating means and a pair of arm members each having an end portion attached to each opposed, flat side wall, said actuating means moving said front and opposed, flat side walls through said pair of arm members between a closed position and an open position.

4. An electrode according to claim 3, wherein said actuating means is a pneumatic cylinder and piston.

5. A measuring apparatus for ascertaining the electrical impedance of a sample of material by radiating an electrical field therethrough, comprising:
    a sample box including front, rear and a pair of opposed, flat side walls of conductive material, having an inlet at one end thereof for receiving a sample of material whose electrical impedance is to be measured, and an outlet situated at the other end of said sample box for exhausting said sample of material from said sample box after its electrical impedance has been measured;
    a flat electrode plate of conductive material situated within said sample box, and disposed with its surfaces substantially equidistant from and parallel with said opposed, flat side walls, said electrode plate being electrically insulated from the walls forming said sample box; and
    a sensing circuit means, electrically connected to said electrode plate for radiating an electrical field through said sample of material, having an output signal which is proportional to the impedance of the sample of material.

6. A measuring apparatus according to claim 5, wherein said sample box has an open and a closed position, and wherein said front wall extends between said pair of opposed, flat side walls to form a substantially rigid front member which is pivotally mounted on a backing plate, said backing plate forming the rear wall of said sample box, so that said front member can be opened outwardly near the outlet end of said sample box, a trap door pivotally mounted on said backing plate near the outlet end of said sample box, so that with said sample box in its closed position, the outlet end of said sample box is substantially sealed, and with said sample box in its open position, said outlet end is open to exhaust material in the sample box therefrom.

7. A measuring apparatus according to claim 6, further including a support frame mounted to hold said sample box in a substantially vertical orientation, a suspension system between said support frame and said backing plate of said sample box, adapted to allow free vertical displacement of said rear wall with respect to said support frame, and a weight measuring means mounted on said backing plate and contacting said support frame so that all of the weight of said sample box is supported by said weight measuring means.

8. A measuring apparatus according to claim 5, further including temperature sensor means providing an output signal proportional to the temperature of said sample of said material; and, temperature circuit means responsive to said output signal from said temperature sensor means for compensating said output signal from said sensing circuit means for variations in temperature of said sample of material.

9. A measuring apparatus according to claim 8, wherein said temperature circuit means includes a signal shaping circuit means converting said output signal from said temperature sensor means to an output signal having a temperature related dependence; and, multiplier circuit means for multiplying said output signal from said sensing circuit means by said output signal from said signal shaping circuit means.

10. A measuring apparatus according to claim 8, further comprising display means responsive to said output signal from said temperature sensor means for visually displaying the temperature of said sample of material.

11. A measuring apparatus according to claim 5, further comprising weight measuring means providing an output signal proportional to the weight of said sample of material; and, bulk density circuit means responsive to said output signal from said weight measuring means for compensating said output signal from said sensing circuit means for variations in bulk density of said sample of material.

12. A measuring apparatus according to claim 11, wherein said bulk density circuit means includes a signal shaping circuit means converting said output signal from said weight measuring means to an output signal having a weight-related dependence; and, multiplier circuit means for multiplying said output signal from said sensing circuit means by said output signal from said signal shaping circuit means.

13. A measuring apparatus according to claim 11, further comprising display means responsive to said output signal from said weight measuring means for visually displaying the weight of said sample of material.

14. A measuring apparatus for measuring the characteristics of a sample of material, comprising:
 a sample box having a substantially constant volume and including: front, rear, and a pair of opposed, flat side walls of conductive material, together forming a rectangular container in which material to be tested is deposited; an inlet means situated at one end of said sample box, including an opening which is sized to received a sample of material therethrough; an outlet means situated at the other end of said sample box, adapted to exhaust the sample of material after its characteristics have been measured; and, a flat electrode plate of conductive material mounted within said sample box and situated with its surfaces substantially parallel with and substantially equidistant from said opposed, flat side walls, said electrode plate being electrically insulated from the walls forming said sample box;
 bulk density means connected to said sample box for determining the bulk density of said sample of material by measuring the weight of said sample of material within said sample box, and including a readout means providing a visual indication of the weight of said sample of material within said sample box; and,
 moisture measuring means interconnected with said flat electrode plate in said sample box and with said bulk density means, and having an output signal which is proportional to the moisture content of said sample of material and which is compensated for variations in bulk density of said sample of material.

15. A measuring apparatus according to claim 14, wherein said sample box is particularly adapted for the discrete sampling of wood chips or the like, and wherein said front and pair of opposed, flat side walls of said sample box form a substantially rigid front member which is pivotally mounted to a backing plate at said one end of said sample box, said backing plate forming said rear wall of said sample box, whereby said front member can be rotated outwardly near said other end of said sample box to define respective closed and open positions of said sample box; and, wherein said bulk density means is operative with said sample box in its closed position so that the static weight of said wood chips within said sample box is visually indicated by said readout means.

16. A measuring apparatus according to claim 14, further comprising temperature means connected to said sample box for determining the temperature of said sample of material in said sample box, and including a readout means providing a visual indication of said temperature, and wherein said moisture measuring means is further interconnected with said temperature means to provide said output signal which is further compensated for variations in temperature of said sample of material.

17. A measuring apparatus according to claim 16, wherein said sample box is particularly adapted for the discrete sampling of wood chips or the like, and wherein said front wall and said pair of opposed, flat side walls of said sample box form a substantially rigid front member which is pivotally mounted to a backing plate at said one end of said sample box, said backing plate forming said rear wall of said sample box, whereby said front member can be rotated outwardy near said other end of said sample box to define respective closed and open positions of said sample box; and, wherein said bulk density means and said temperature means are operative when said sample box is in its closed position so that the static weight and temperature of said wood chips within said sample box are visually indicated by said readout means respectively within said bulk density means and said temperature means.

* * * * *